United States Patent [19]

Tanger

[11] Patent Number: 4,485,254
[45] Date of Patent: Nov. 27, 1984

[54] PROCESS FOR PREPARING PHENOXYBENZOIC ACIDS

[75] Inventor: Charles M. Tanger, Levittown, Pa.

[73] Assignee: Rohm and Haas Company, Philadelphia, Pa.

[21] Appl. No.: 306,990

[22] Filed: Sep. 30, 1981

Related U.S. Application Data

[62] Division of Ser. No. 931,054, Aug. 4, 1978, Pat. No. 4,393,692.

[51] Int. Cl.$^3$ ............................................. C07C 79/46
[52] U.S. Cl. ..................................... 560/21; 562/438; 260/455 R; 564/180; 564/166
[58] Field of Search .................... 560/21; 260/455 R; 564/166

[56] References Cited

U.S. PATENT DOCUMENTS 3,784,635  1/1974  Theissen ............................... 560/21
3,928,416  12/1975  Bayer et al. ............................ 560/21

FOREIGN PATENT DOCUMENTS 3416  1/1979  European Pat. Off. .............. 560/21

OTHER PUBLICATIONS

Scarborough, H. A. et al., J. of Chem. Soc., 1934 (52–56).

Primary Examiner—Paul J. Killos
Attorney, Agent, or Firm—Terence P. Strobaugh

[57] ABSTRACT

This process relates to the oxidation of phenoxytoluenes to phenoxybenzoic acids utilizing a hydrogen peroxide activated, bromide promoted cobalt catalyst which can be performed at atmospheric pressure and at moderate temperatures. These phenoxybenzoic acids can then be esterified and selectively nitrated to give the corresponding 2-nitro-5-(substituted)phenoxybenzoic acid esters. Alternatively the acids can be nitrated and then esterified.

7 Claims, No Drawings

PROCESS FOR PREPARING PHENOXYBENZOIC ACIDS

This is a division of application Ser. No. 931,054 filed Aug. 4, 1978 now U.S. Pat. No. 4,393,692.

SUMMARY OF THE INVENTION

This invention relates to an improved process for the preparation of phenoxybenzoic acids and derivatives thereof having the formula

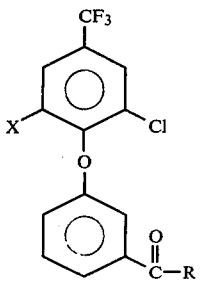

wherein R is OR$^1$, SR$^1$, NR$^1$R$^1$ wherein R$^1$ is hydrogen, alkyl, substituted alkyl or alkenyl, and X is hydrogen or halogen which comprises oxidizing a phenoxytoluene of the formula

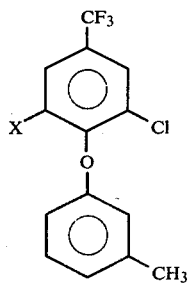

in an appropriate protic solvent in the presence of a cobalt catalyst, a bromide catalyst promoter, a hydrogen peroxide catalyst activator and molecular oxygen at atmospheric pressure and moderate temperatures from about 70° C. to about 115° C.

BACKGROUND OF THE INVENTION

The autoxidation of aralkyl hydrocarbons to aromatic carboxylic acids utilizing a cobalt acetate catalyst is known in the art. It is reported in the literature that various agents can be utilized to activate the cobalt acetate catalyst. A. S. Hay and H. S. Blanchard reported in the *Canadian Journal of Chemistry* vol. 43, 1306-1317 (1965) that the addition of bromide ion produces a highly active cobalt acetate catalyst. E. I. Heiba et al. reported in the *Journal of the American Chemical Society* vol. 91, 6830-6837 (1969) that the addition of lithium chloride yielded arylaldehydes and rearrangement products due to the effect of the chloride ion. However, the oxidation to an arylcarboxylic acids is not reported therein. The U.S. Pat. Nos. 3,665,030 granted May 23, 1972 and 3,969,405 granted July 13, 1976 to Pierre de Radzitzky d'Ostrowick and Jacques D. V. Hanotier disclose the selective oxidation of aralkyl hydrocarbons to aldehydes, ketones and carboxylic acids utilizing a cobalt acetate catalyst activated with various acids.

It is reported in Agdoc 73094u that Japanese Pat. No. 48661450 granted Aug. 28, 1973 to Sumitomo Chemical Industry Company Limited discloses the preparation of meta-phenoxybenzoic acid utilizing acetaldehyde as an activator for the cobalt acetate catalyst. U.S. Pat. No. 3,519,684 granted July 7, 1970 to Enrique R. Witt et al. discloses that peracetic acid can be used to activate cobalt acetate in the high pressure and temperature oxidation of dialkyl aromatic compounds to aromatic dicarboxylic acids.

DETAILED DESCRIPTION OF THE INVENTION

This invention relates to an improved process utilizing atmospheric pressure, moderate temperatures and hydrogen peroxide via a cobalt catalyst activator. In particular, this invention relates to the preparation of phenoxy benzoic acids and derivatives thereof having the formula

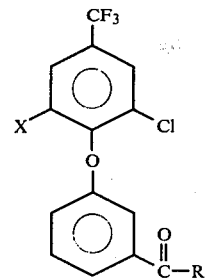

wherein R is OR$^1$, SR$^1$, NR$^1$, R$^1$ and R$^1$ is hydrogen, alkyl, substituted alkyl or alkenyl preferably hydrogen or alkyl of from 1 to 4 carbon atoms which may be straight or branched chain and X is hydrogen or halogen preferably hydrogen or chlorine which comprises oxidizing a phenoxytoluene of the formula

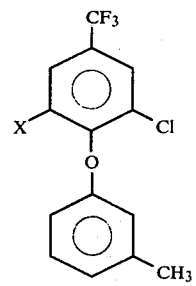

wherein X is hydrogen or halogen preferably hydrogen or chlorine in an appropriate protic solvent in the presence of a cobalt catalyst, a bromide catalyst promoter or a compound capable of liberating bromide ion under oxidation conditions, a hydrogen peroxide catalyst activator and molecular oxygen at temperatures from about 70° C. to about 115° C. and atmospheric pressure.

In the above process, typical protic solvents that can be utilized include acetic acid, propionic acid butyric acid and the like. Acetic acid is the preferred solvent.

The concentration of substrate (Formula II) in the reaction solvent is from about 0.1 to about 10 moles of substrate per liter of solvent. A preferred concentration is from about 1 to about 8, more preferably from about 1 to about 6 moles of substrate per liter of solvent.

The cobalt (II) salts that can be utilized in this oxidation process include cobaltous salts wherein the anion is selected to satisfy the valence charge of the cobalt cation and is selected so that the cobaltous cation Co(II) can be readily oxidized in situ to the more reactive cobaltic cation, Co(III), by an appropriate activator. Typical cobaltous salts include cobaltous acetate, cobaltous propionate, cobaltous naphthenate, cobaltous bromide and the like in either the anhydrous or hydrated forms. The preferred cobaltous salt is cobaltous acetate tetrahydrate.

The concentration of cobalt catalyst, charged as the cobalt (II) salt, per mole of substrate is from about 0.001 to about 0.5 mles per mole of substrate, preferably from about 0.01 to about 0.24 more preferably from about 0.03 to about 0.12 moles of cobalt (II) salt per mole of substrate.

The catalyst promoter utilized in the process of this invention is the bromide ion. The source of the bromide ion promoter can be from hydrogen bromide either anhydrous or aqueous, sodium bromide, ammonium bromide, potassium bromide and the like. The preferred source is aqueous hydrogen bromide.

The ratio of bromide ion per mole of Cobalt (II) salt is from about 1 to about 3 equivalents per mole of Cobalt (II) salt, preferably from about 1 to about 2 equivalents per mole of Cobalt (II) salt, more preferably about one equivalent per mole of Cobalt (II) salt.

Hydrogen peroxide is utilized as a cobalt salt activator readily oxidizing the Co(II) to the required Co(III) state, thus enabling the reaction to be run at lower temperature and pressures than previously reported. The ratio of hydrogen peroxide per mole of Cobalt (ii) salt is from about ½ to about 1 mole per mole of cobalt (II) salt. A preferred concentration of the aqueous hydrogen peroxide source is from about 3 to about 90%, more preferably about 30 to 35%, aqueous solution.

The presence of a source of molecular oxygen is also needed in this process. The concentration of oxygen in the source can be from about 10% to about 100%. The carrier gas associated with the molecular oxygen can be any inert gas such as nitrogen, or the like. Compressed air is a preferred source for the molecular oxygen.

The molecular oxygen feed rate will affect the rate of reaction. Feed rates of from about 0.001 to about 1.0 moles of oxygen per minute per mole of phenoxytoluene can be utilized. Rates of from about 0.003 to about 0.1 are preferred and the most preferred rate is from about 0.008 to 0.03 moles of oxygen per minute per mole of phenoxytoluene.

Temperatures utilized for the process of this invention are from about 70° C. to about 115° C. preferably from about 90° C. to about 110° C.

The process of this invention can be performed by either a continuous or a batch process. The reagents used in this oxidation process can be combined in any order. Preferably, all charges except the hydrogen peroxide and source of molecular oxygen are made to the reactor followed by addition of the hydrogen peroxide just prior to or immediately following the initiation of the molecular oxygen feed.

Since the oxidation product obtained in this process is a carboxylic acid, the alkali metal salts and alkyl esters of the carboxylic acid can be prepared by standard techniques known in the art and can also be utilized to isolate or purify the oxidation product.

The acid or the ester can also be nitrated at temperatures from 0° to about 70° C. Any conventional electrophilic nitrating agent can be used. However, the preferred nitrating agents include nitric acid/sulfuric acid, potassium nitrate/sulfuric acid, or nitric acid/sulfuric acid/acetic anhydride. An optional solvent, such as methylene dichloride, ethylene dichloride, chloroform, perchloroethylene and the like can also be used.

Once the carboxylic acid is prepared it can be converted to derivatives such as the acid halide, the alkyl, substituted alkyl or alkenyl esters, the thio esters or the amides via general synthetic routes well known in the art. For example the alkyl, substituted alkyl and alkenyl esters can be prepared by reacting the carboxylic acid with the appropriate alkyl substituted alkyl or alkenyl, alcohol in an inert solvent in the presence of an acid catalyst. The thio esters and amides can be prepared by reacting the acid halide with an appropriate mercaptan or amine in an inert solvent.

The alkali metal salts of the carboxylic acids are prepared by treating the carboxylic acid with an alkali metal hydroxide or hydride such as sodium hydroxide, potassium hydroxide, sodium hydride and the like in an inert solvent.

The following examples are presented to further illustrate the process of this invention and are not intended to limit the breadth and scope of this invention in any way.

EXAMPLE I

1. Preparation of 3-(2-chloro-4-trifluoromethylphenoxy)toluene

Dimethyl sulfoxide (975 g) and meta-cresol (113.3 g, 1.05 moles) are charged to a 2-1, 3-neck round bottom flask equipped with a mechanical stirrer, thermometer, and a 5-plate Oldershaw column with a variable reflux ratio distillation head. A 50% potassium hydroxide solution (119.0 g, 1.06 moles) is added over 2 minutes and is accompanied by an exotherm from 25° C. to 41° C. Water is removed by distillation under vacuum to a final vapor temperature of 105° C. at a pressure of 50 mm Hg. A total of 375 ml of distillate is collected.

The solution is cooled to 80° C. and 3,4-dichlorobenzotrifluoride (215.0 g, 1.00 mole) is added. The reaction mixture is heated to 140° C. over a 6 hour period and then held at 140° C. for 2½ hours.

The DMSO solvent is removed by vacuum distillation at 120° C. to a final pressure at 25 mm Hg. The resulting reaction product is diluted with 150 ml of perchloroethylene. The organic solution is washed with 350 ml of 5% NaOH, 350 ml of water, and concentrated on a rotary evaporator to give 289.9 g of product which analyzes for 81.6% of 3-(2-chloro-4-trifluoromethylphenoxy)toluene. The A.I. yield is 89.4% with a 4.5% yield of the isomeric 3-(2-chloro-5-trifluoromethylphenoxy)toluene.

2. Cobalt-catalyzed oxidation of 3-(2-chloro-4-trifluoromethylphenoxy)toluene to 3-(2-chloro-4-trifluoromethylphenoxy)benzoic acid Into a three liter flask is added 1.3 liters of acetic acid, 614 g. (1.90 mole) of 88.8% pure 3-(2-chloro-4-trifluoromethylphenoxy)toluene, and 32.0 g. (0.128 mole) of cobalt acetate tetrahydrate. To this stirred pink solution is added 20.0 ml (0.173 mole) of 47% aqueous hydrogen bromide whereupon the solution turns blue. The solution is then heated to 90° C. and a flow of oxygen (100%, 2.19×10⁻² mole/min) is initiated. Hydrogen peroxide 10.0 ml (30%, 0.088 mole) is then added via a syringe to the solution and the exotherm raises the reaction temperature to 98° C. within 5 minutes. The reaction is monitored by thin layer chromatography and is complete within 4 hours. Isolation of the oxidation product 3-(2-chloro-4-trifluoromethylphenoxy)benzoic acid from the reaction mixture is accomplished by distillation of the acetic acid solvent, neutralization with aqueous sodium hydroxide to a pH of 11, filtration to remove the insoluble cobalt hydroxides and acidification of the filtrate with sulfuric acid to precipitate the product, which is filtered and dried to give 680.3 g of 85.1% 3-(2-chloro-4-trifluoromethylphenoxy)benzoic acid. This represents of 96.1% yield of this product based on the 3-(2-chloro-4-trifluoromethylphenoxy)toluene starting material.

It is to be understood that changes and variations of this process such as the addition of various additional metal salts to reduce solvent degradation or increase purity or yield may be made without departing from the spirit and scope of the invention as defined by the appended claims.

I claim:

1. A process for preparing a compound of the formula:

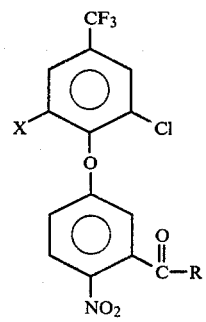

wherein R is ONa, OR¹, SR¹, or NR¹R¹ wherein R¹ is hydrogen, alkyl, substituted alkyl or alkenyl, and X is hydrogen or halogen which comprises oxidizing a phenoxytoluene in an appropriate protic solvent in the presence of a cobalt catalyst, a hydrogen peroxide catalyst activator and molecular oxygen at temperatures from about 70° C. to about 115° C. to a phenoxybenzoic acid and nitrating the phenoxybenzoic acid using a nitrating agent selected from nitric acid/sulfuric acid, potassium nitrate/sulfuric acid or nitric acid/sulfuric acid/acetic anhydride at temperatures from 0° to about 70° C. to produce the nitrophenoxybenzoic acid.

2. A process for preparing a compound of the formula:

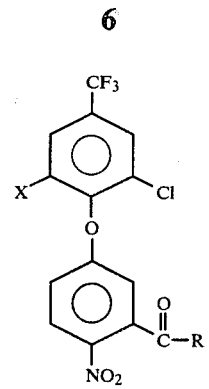

wherein R is ONa, OR¹, SR¹, or NR¹R¹ wherein R¹ is hydrogen, alkyl, substituted alkyl or alkenyl, and X is hydrogen or halogen, which comprises reacting an alkali metal salt of m-cresol with a substituted phenyl halide to produce a 3-(substituted phenoxy)-toluene, oxidizing the phenoxytoluene in an appropriate protic solvent in the presence of a cobalt catalyst, a hydrogen peroxide catalyst activator and molecular oxygen at temperatures from about 70° C. to about 115° C. to a phenoxybenzoic acid and nitrating the phenoxybenzoic acid using a nitrating agent selected from nitric acid/sulfuric acid, potassium nitrate/sulfuric acid or nitric acid/sulfuric acid/acetic anhydride at temperatures from 0° to about 70° C. to produce the nitrophenoxybenzoic acid optionally followed by esterification, amidation or salt formation.

3. The process of claim 2 wherein the alkali metal salt of m-cresol is produced by reacting m-cresol with an alkali metal base.

4. A process for preparing a compound of the formula:

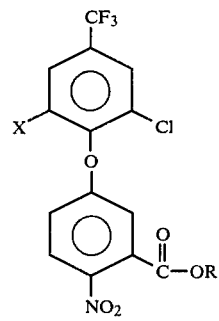

wherein X is a hydrogen or halogen atom and R is hydrogen, sodium alkyl, substituted alkyl or alkenyl, which comprises:

(a) forming a salt of m-cresol;
(b) reacting the salt of m-cresol with 3,4-dichlorobenzotrifluoride to form a 3-(2-chloro-4-trifluoromethylphenoxy)toluene;
(c) oxidizing the phenoxytoluene of step (b) in an appropriate protic solvent in the presence of a cobalt catalyst, a hydrogen peroxide catalyst activator and molecular oxygen at temperatures from about 70° C. to about 115° C. to form a 3-(2-chloro-4-trifluoromethylphenoxy)benzoic acid; and
(d) nitrating the benzoic acid of step (c) using a nitrating agent selected from nitric acid/sulfuric acid, potassium nitrate/sulfuric acid or nitric acid/sulfuric acid/acetic anhydride at temperatures from 0° to about 70° C. to form a 2-nitro-(2-chloro-4-trifluoromethylphenoxy)benzoic acid.

5. The process of claim 2 or claim 4 wherein the step of oxidizing the phenoxytoluene to a phenoxybenzoic acid is conducted in an appropriate protic solvent selected from the group consisting of acetic acid, proprionic acid and butyric acid in the presence of from about 0.001 to about 0.5 moles of a cobalt (II) salt per mole of phenoxytoluene, from about 1 to about 3 equivalents of bromide ion per mole of cobalt (II) salt, from about 0.5 to about 1 mole of a 30 to 35% aqueous solution of hydrogen peroxide per mole of cobalt (II) salt and a feed rate of from about 0.1 to about 0.003 moles of about a 10% to about a 100% molecular oxygen gas source per mole of phenoxytoluene, at temperatures from about 70° C. to about 115° C., at about atmospheric pressure to form the phenoxybenzoic acid.

6. The process of claim 4 wherein the acid of step (d) is converted into an alkali metal salt.

7. The process of claim 4 wherein the acid of step (c) or the acid of step (d) is esterified with an alkanol.

* * * * *